(12) United States Patent
Bordas

(10) Patent No.: US 10,524,889 B1
(45) Date of Patent: Jan. 7, 2020

(54) SALIVA EVACUATOR SYSTEM AND SALIVA EVACUATOR TIP ASSEMBLY INCLUDING A TRANSVERSE ON/OFF PUSH VALVE

(71) Applicant: Ildefonso Anthony Bordas, Huntington Beach, CA (US)

(72) Inventor: Ildefonso Anthony Bordas, Huntington Beach, CA (US)

(*) Notice: Subject to any disclaimer, the term of this patent is extended or adjusted under 35 U.S.C. 154(b) by 37 days.

(21) Appl. No.: 15/593,032

(22) Filed: May 11, 2017

Related U.S. Application Data

(63) Continuation-in-part of application No. 13/523,151, filed on Jun. 14, 2012, now abandoned.

(51) Int. Cl.
| | | |
|---|---|---|
| *A61M 1/08* | (2006.01) | |
| *A61C 17/08* | (2006.01) | |
| *A61M 1/00* | (2006.01) | |

(52) U.S. Cl.
CPC ............ *A61C 17/08* (2019.05); *A61M 1/008* (2013.01); *A61M 1/0043* (2013.01)

(58) Field of Classification Search
CPC .... A61C 17/043; A61C 17/08; A61M 1/0043; A61M 1/008; A61M 1/0001–14
USPC ............... 433/95, 96; 604/19; 251/319, 326
See application file for complete search history.

(56) References Cited

U.S. PATENT DOCUMENTS

| | | | | |
|---|---|---|---|---|
| 2,790,190 A | * | 4/1957 | Mastrandrea | ...... A46B 11/0017 401/188 R |
| 4,451,257 A | * | 5/1984 | Atchley | .............. A61M 1/0043 251/325 |
| 2014/0141383 A1 | * | 5/2014 | Hagelganz | ............. A61C 7/287 433/9 |

* cited by examiner

*Primary Examiner* — Yogesh P Patel
(74) *Attorney, Agent, or Firm* — John Rizvi; John Rizvi, P.A.-The Patent Professor ®

(57) ABSTRACT

The present invention provides a saliva evacuator system for removing saliva, and optionally debris, from the mouth of a dental patient. The saliva evacuator system includes a vacuum pump, a flexible tubing connected at one end to the vacuum pump, and a tip assembly at the other end of the tubing, the tip assembly carrying a vacuum on/off valve. The on/off valve is positioned so that the on/off valve remains outside of the patient's mouth when the tip assembly is inserted into the patient's mouth. The on/off valve is a single-piece body push valve that is transversely movable within a hollow body of the tip assembly and is retained on the hollow by opposite ends of the on/off valve. One end of the on/off valve preferably clips onto the hollow body. The tip assembly can include a saliva ejector tip, a high-volume evacuator tip or a surgical high-volume evacuator tip.

18 Claims, 9 Drawing Sheets

SALIVA EVACUATOR SYSTEM AND SALIVA EVACUATOR TIP ASSEMBLY INCLUDING A TRANSVERSE ON/OFF PUSH VALVE

CROSS-REFERENCE TO RELATED APPLICATION

This application is a Continuation-In-Part (CIP) of U.S. Utility patent application Ser. No. 13/523,151, filed on Jun. 14, 2012, which is incorporated by reference herein in its entirety.

FIELD OF THE INVENTION

The present invention relates generally to dental systems, and more particularly, to a saliva evacuator system and saliva evacuator tip assembly in which a hollow tip body has a single-piece valve transversely movably attached to the tip body and configured to allow or block fluid flow through the tube.

BACKGROUND OF THE INVENTION

Surgical procedures carried out in the area of a patient's mouth must include the constant removal of saliva and, frequently, additional fluids or debris in order for the medical practitioner to be able to have good visibility and access to the surgical site. For this purpose, apparatus known as saliva evacuators have been developed. Saliva evacuators generally include a vacuum pump. A first end of a flexible hose is in fluid communication with the vacuum pump, and a suction tip is in turn removably attached to the opposite end of the flexible hose, often via an adapter. The on/off valve is typically arranged between the vacuum pump and the flexible hose. Operation of the pump causes liquids, and optionally other substances, to be aspirated from the patient's oral cavity, suctioned through the suction tip and flexible hose, and disposed into a container or other applicable destination. Often, saliva evacuators are provided with an on/off valve which can be operated by the dental practitioner to allow or block fluid from passing from the flexible hose to the container or other applicable destination. When the dental practitioner no longer needs vacuum suction, he/she will shut the valve or switch off the vacuum pump.

For example, a first type of saliva evacuator, commonly referred to as saliva ejector system, is known in the prior art for the purpose of suctioning liquids, but not particles, from the oral cavity. The flexible hose of a saliva ejector system is generally narrow, i.e. has a small diameter. The suction tip, or saliva ejector tip, is also generally narrow.

A second type of saliva evacuator, often referred to as a high volume evacuator (HVE), allows to suction both liquids and particles form the oral cavity. The flexible hose and suction tip are wider than those of a saliva evacuator. Due to the larger diameters, high volume evacuators are able to remove larger particles from the oral cavity and have a greater volume capacity. In addition, the suction tip of the high volume evacuator is generally non-flexible.

Surgical high-volume evacuators are also known in the prior art, and generally include a large diameter hose (the same hose as the high volume evacuator described above) connected to a vacuum pump. The only difference between a surgical high-volume evacuator and a high volume evacuator is the suction tip. In a surgical high-volume evacuator, the non-flexible suction tip tapers to a smaller diameter at the distal end or tip. This allows the use of high volume suction for procedures that require difficult access (such as surgical and endodontic procedures). The surgical high-volume evacuator has the same volume capacity as a high volume evacuator (HVE), while the tapered tip allows gaining access and improving maneuverability in the oral cavity.

After being used with a patient, saliva evacuators known in the art require disassembly, lubrication and sterilization prior to their use with a following patient. Specifically, the valve is disconnected from the vacuum pump and manually sterilized, while the suction tip and the flexible hose are disconnected from the valve and disposed. Once the valve is sterilized, it is attached to the vacuum pump, and a new flexible hose and suction tip are attached to the valve. As those skilled in the art will understand, sterilizing is a time-consuming, cumbersome and expensive process.

Accordingly, there is an established need for a saliva evacuator which solves at least one of the aforementioned problems. Particularly, there remains a need for a saliva evacuator which does not require sterilization of an on/off valve between uses.

SUMMARY OF THE INVENTION

The present invention is directed to a saliva evacuator system for oral fluid evacuation, to be used for instance as a saliva ejector, high volume evacuator or surgical high-volume evacuator during dental operatory and surgical applications. The saliva evacuator system includes a suction tip or tip assembly comprising a hollow tip body and an on/off valve extending transversely through the hollow tip body. The on/off valve is formed as a single-piece unit, extends transversely through the tip body and can be pushed transversely and reversibly from a closed position to an open position. In both the open and closed positions, a respective end of the on/off valve rests on a sidewall of the tip body, retaining or locking the on/off valve within the tip body and preventing it from being removed from the tip body. Preferably, the on/off valve clips onto the tip body by at least one elastically deformable clipping arm situated at one of the ends of the on/off valve. The tip assembly is easy to assemble and can be manufactured at reasonable cost, yet is robust and resistant to repeated operation of the on/off valve. The tip assembly can be disposable, thus preventing cross-contamination between patients and avoiding having to sterilize the device between patients.

In a first implementation of the invention, a saliva evacuator system for removing saliva from a patient's mouth includes a vacuum pump, a tubing connected to the vacuum pump, and a hollow tip assembly removably attachable to a distal end of the tubing. The tip assembly comprises a hollow tip body delimiting an internal space. The internal space extends in a longitudinal direction through a length of the tip body from a proximal end of the tip body to a distal end of the tip body. The tip assembly further comprises an on/off valve formed as a single-piece body movably extending through the tip body transversely to the longitudinal direction. The on/off valve has a first end, an opposite, second end and a through hole. The saliva evacuator system is configured to selectively and reversibly adopt an open position and a closed position, by transversely moving the on/off valve relative to the tip body. In the open position, the on/off valve is moved to a first transverse position relative to the tip body in which the through hole of the on/off valve is longitudinally aligned with the internal space of the tip body allowing fluid to pass therethrough, and further in which the on/off valve protrudes from opposite transverse sides of the tip body and the first end of the on/off valve rests against the tip body stopping the on/off valve from being removed from the tip body. In the closed position, the on/off valve is moved to a second transverse position relative to the tip body in which the through hole of the on/off valve is out of longitudinal alignment with the internal space of the tip body and a solid portion of the on/off valve is longitudinally aligned with said internal space, preventing fluid from passing therethrough, and further in which the on/off valve protrudes from opposite transverse sides of the tip body and the second end of the on/off valve rests against the tip body stopping the on/off valve from being removed from the tip body.

In another implementation of the invention, a tip assembly for a saliva evacuator system for removing saliva from a patient's mouth comprises a hollow tip body delimiting an internal space. The internal space extends in a longitudinal direction through a length of the tip body from a proximal end of the tip body to a distal end of the tip body. The tip assembly further includes an on/off valve formed as a single-piece body movably extending through the tip body transversely to the longitudinal direction. The on/off valve has a first end, an opposite, second end and a through hole. The tip assembly is configured to selectively and reversibly adopt an open position and a closed position by transversely moving the on/off valve relative to the tip body. In the open position, the on/off valve is moved to a first transverse position relative to the tip body in which the through hole of the on/off valve is longitudinally aligned with the internal space of the tip body allowing fluid to pass therethrough, and further in which the on/off valve protrudes from opposite transverse sides of the tip body and the first end of the on/off valve rests against the tip body stopping the on/off valve from being removed from the tip body. In the closed position, the on/off valve is moved to a second transverse position relative to the tip body in which the through hole of the on/off valve is out of longitudinal alignment with the internal space of the tip body and a solid portion of the on/off valve is longitudinally aligned with said internal space, preventing fluid from passing therethrough, and further in which the on/off valve protrudes from opposite transverse sides of the tip body and the second end of the on/off valve rests against the tip body stopping the on/off valve from being removed from the tip body.

In another aspect, the on/off valve can be formed as a single-piece body by plastic injection molding.

In another aspect, the second end of the on/off valve can include at least one elastically flexible clipping arm configured to flex inward allowing the on/off valve to be inserted through the tip body and elastically biased to return to an outward position for the resting of the clipping arm on the tip body when the tip assembly is in the closed position. In some embodiments, the on/off valve includes two elastically flexible clipping arms arranged on respective opposite sides of the second end of the on/off valve, preferably facing away from one another.

In another aspect, the tip body can include one of a saliva ejector tip, a high-volume evacuator tip and a surgical high volume evacuator tip. The tip assembly can optionally include different tip portions which can be interchangeably attached to a valve support portion of the tip body.

In another aspect, the tip body can include a valve support portion and a top portion, wherein the valve support portion carries the on/off valve and the tip portion is removably attached to the valve support portion.

In another aspect, the tip body can include a valve support portion and a first tip portion, wherein the valve support portion carries the on/off valve and the first tip portion is removably attached to the valve support portion. The tip portion can be a saliva ejector tip, a high-volume evacuator tip or a surgical high volume evacuator tip.

In another aspect, the tip body can include a valve support portion and two or more tip portions, wherein the valve support portion carries the on/off valve and the two or more tip portions are removably and interchangeably attachable to the valve support portion. The two or more tip portions can include two or more of a saliva ejector tip, a high-volume evacuator tip and a surgical high volume evacuator tip.

In another aspect, an adapter can be removably connectable to the tubing and to the tip body.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a saliva evacuator system comprising a suction tip or tip assembly which includes a hollow tip body and an on/off valve extending transversely through the hollow tip body. The on/off valve is formed as a single-piece body, extends transversely through the tip body and can be pushed transversely and reversibly from a closed position to an open position. In both the open and closed positions, a respective end of the on/off valve rests on a sidewall of the tip body, retaining the on/off valve on the tip body and preventing it from being removed from the tip body. The on/off valve can clip onto the tip body by at least one elastically deformable clipping arm situated at an end of the on/off valve.

Figure 1:
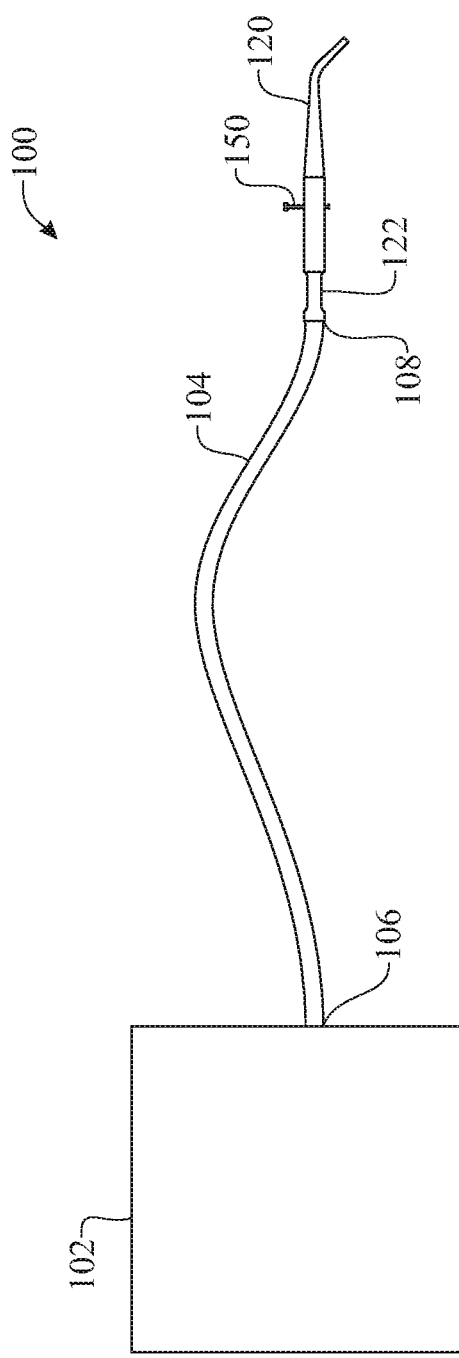
FIG. 1 presents a schematic representation of a saliva evacuator system in accordance with a illustrative embodiment of the present invention.

Referring now to FIG. 1, a saliva evacuator system 100 in accordance with the invention is shown in schematic view. The saliva evacuator system 100 includes a vacuum pump 102, a flexible hose or tubing 104 having a proximal end 106 connected to the vacuum pump 102, and a hollow suction tip or tip assembly 110 removably attachable to a distal end 108 of the tubing 104. The tip assembly 110 comprises an elongated, hollow tip body 120 and an on/off valve 150 located approximately halfway along the tip body 120 in a longitudinal direction of the tip body 120. The tip assembly 110 is attached to the tubing 104 via an adapter 122, which can be metallic and non-disposable. The hollow tip body 120 is in fluid communication with the tubing 104 via the adapter 122 for aspirating fluids from an open, distal end of the tip body 120, through the tip body 120 and into the tubing 104. The on/off valve 150 can be operated by a user to selectively allow or prevent fluid flow from the distal end of the tip body 120 to the tubing 104, as will be described in greater detail hereinafter.

With continued reference to FIG. 1, it must be noted that, in prior art saliva ejector systems, a metallic, shutoff valve would be instead disposed between the vacuum pump and the tubing. To use the system, a dental practitioner would turn on the vacuum pump and open the valve. The tip assembly would then be inserted into the mouth of the patient and saliva would be sucked from the patient's mouth, through the tubing to the vacuum pump. When the dental practitioner no longer needed vacuum suction, he/she would shut the valve. He/she would then open the valve as appropriate to the procedure and the patient. Once the procedure had ended, the tubing and tip assembly would be disconnected and disposed, and the valve would be disconnected, lubricated and sterilized for further use.

Figure 2:
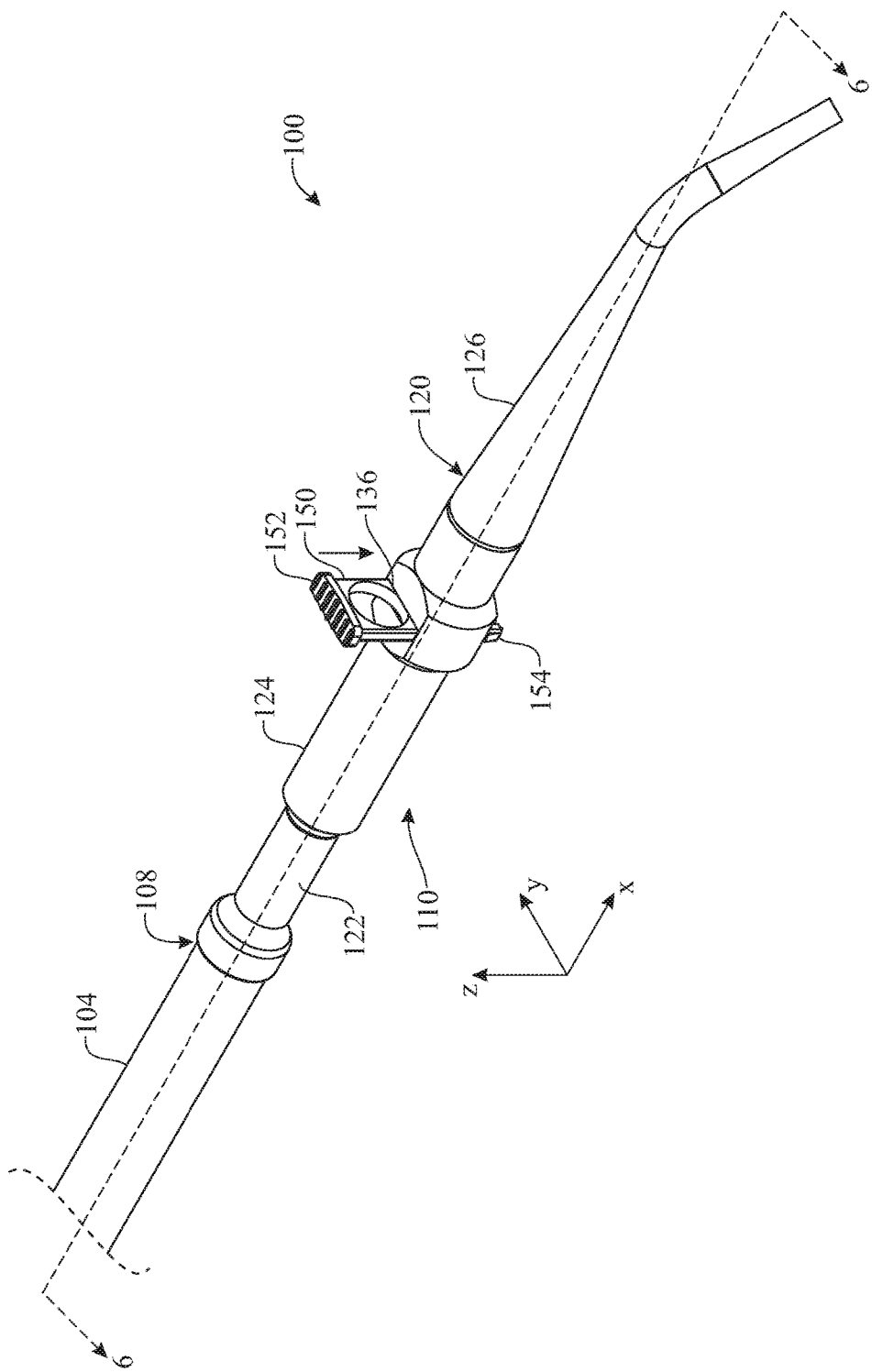
FIG. 2 presents a top front isometric assembled view of a distal end of a saliva evacuator system in accordance with the present invention, including a tip assembly attached to a flexible tubing via an adapter, the tip assembly comprising tip body and an on/off valve, the tip body ending in a tapered ejector tip.
Figure 3:
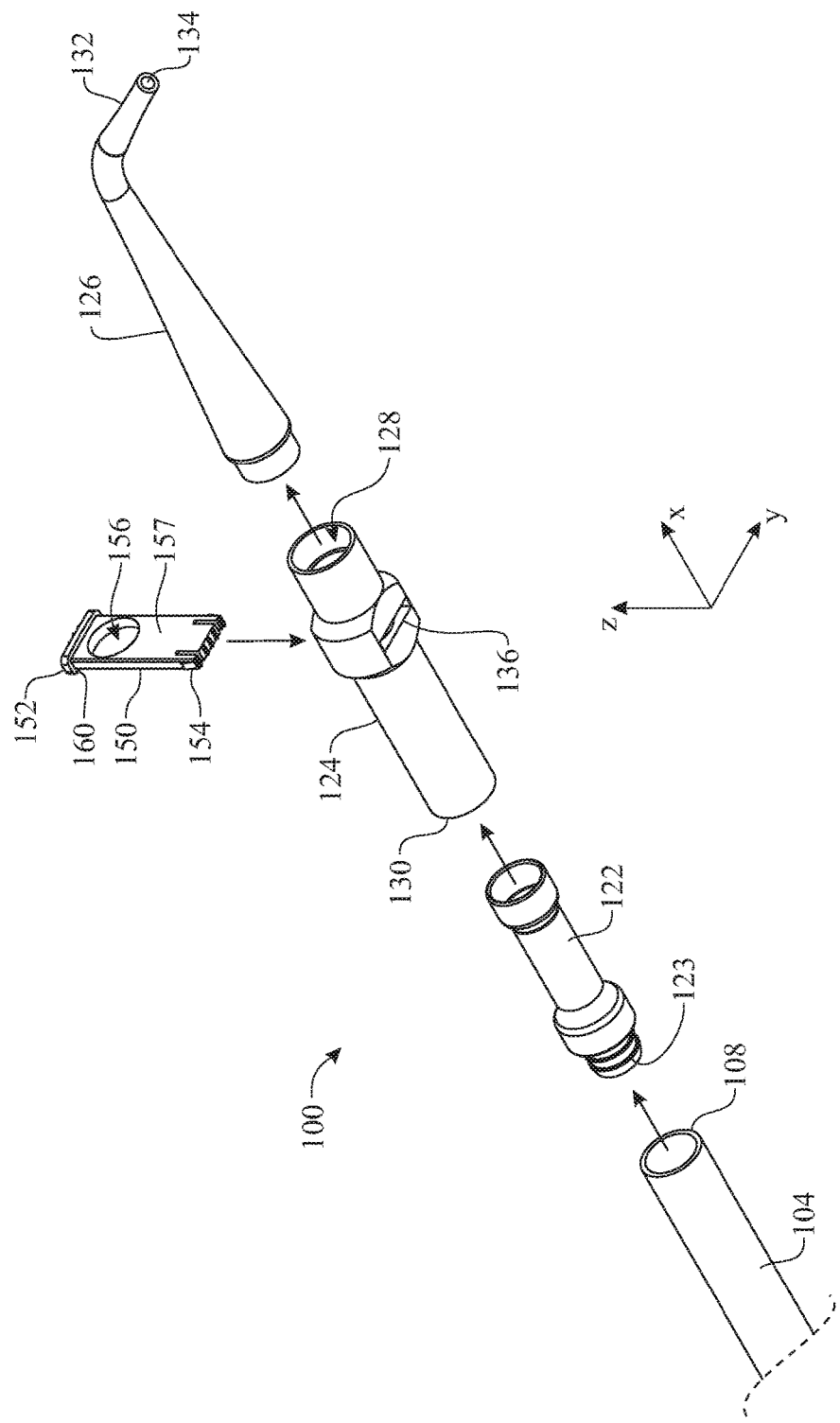
FIG. 3 presents an exploded, bottom front isometric view of the tip assembly, adapter and tubing.

Turning again to the present invention, attention is directed to FIGS. 2 and 3, which illustrate the hollow tip assembly 110 of FIG. 1 in greater detail. As shown, the adapter 122 is disconnectably attached to the distal end 108 of the tubing 104 preferably by friction fit, and can include one or more O-ring seals 123 to provide a watertight male-female fitting of the adapter 122 and the distal end 108 of the tubing 104. In turn, the hollow tip body 120 of the tip assembly 110 can be formed, for instance and without limitation, of two separate body portions which are removably attached to one another. A first body portion or valve support portion 124 is disconnectably attached to the adapter 122, for instance by friction fit. A second body portion or tip portion 126, in turn, is disconnectably attached to the valve support portion 124, for instance by friction fit, and provides a distal end of the hollow tip body 120. The tip portion 126 of the present embodiment has a narrow, tapered distal end designed for situations where the operator requires more precise aspiration in smaller areas; thus, the tip portion 126 shown herein can represent a saliva ejector tip or a surgical high volume evacuator tip. The adapter 122 of the present embodiment allows adapting the valve support portion 124 to a narrower tubing 104 of the kind that are normally used with saliva ejector tips. The two body portions 124 and 126 are hollow and in fluid communication with one another. The tip body 120 is therefore hollow and delimits an internal space 128 therewithin. The internal space 128 extends in a longitudinal direction x through a length of the tip body 120 from a proximal end 130 of the tip body 120 to a distal end 132 of the tip body 120. An opening 134 at the distal end 132 of the tip body 120 allows suctioning fluid into the internal space 128 and towards the tubing 104.

With continued reference to FIGS. 2 and 3, the on/off valve 150 comprised in the tip assembly 110 extends through the tip body 120 in a transverse direction z which is perpendicular to the longitudinal direction x, and is movable back and forth in said transverse direction z. More specifically, the on/off valve 150 extends through opposite side slots 136 formed in the valve support portion 124 of the tip body 120 and through the internal space 128 which extends between the slots 136. As shown, the on/off valve 150 is arranged closer to the proximal end 130 of the tip body 120 than to the distal end 132 of the tip body 120.

Figure 4:
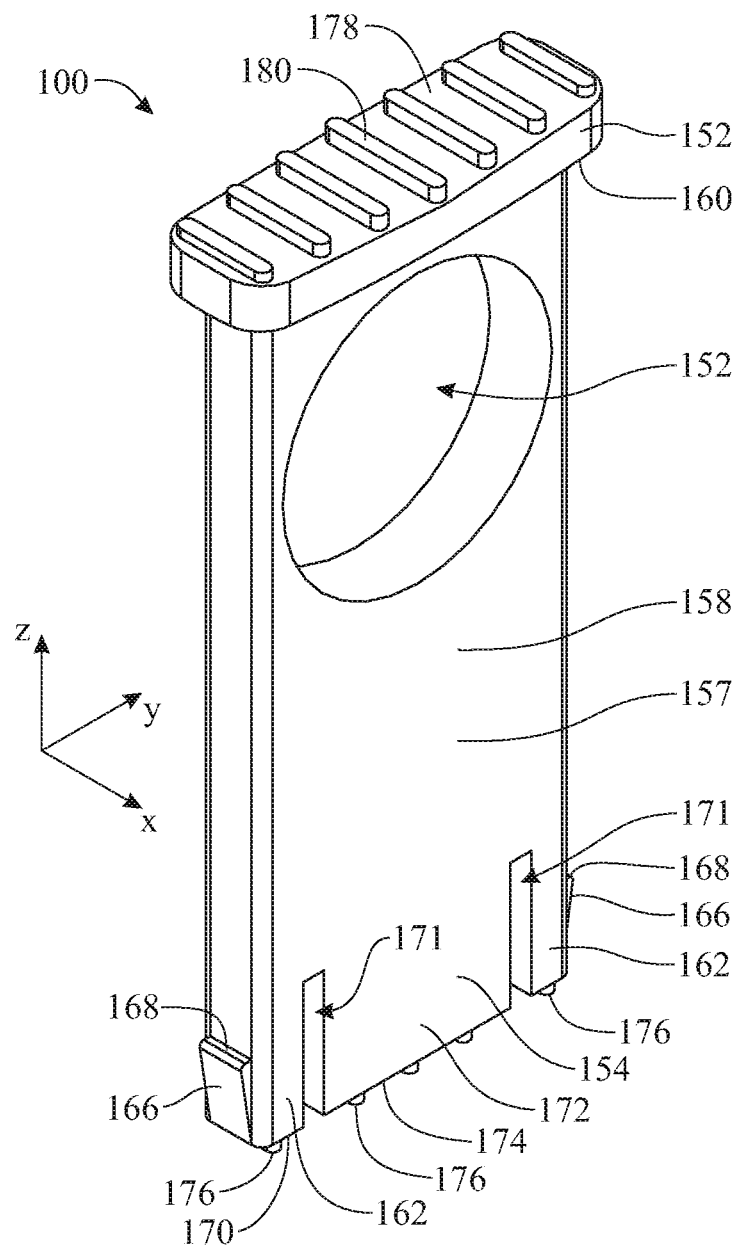
FIG. 4 presents a top front isometric view of the on/off valve of FIG. 2.

As better shown in FIG. 4, the on/off valve 150 is formed as a single-piece body having a first end 152 and an opposite, second end 154. A through hole 156 extends through the single-piece body and is configured to selectively align with the internal space 128 of the tip body 120 for purposes that will be described hereinafter. The on/off valve 150 has a generally rectangular central portion 158. The first end 152 of the on/off valve 150 is arranged at one end of the central portion and is generally wider than the central portion 158 in at least one of the longitudinal direction x and a lateral direction y which is perpendicular to the longitudinal and transverse directions x and z. In some embodiments, such as in the present embodiment, the first end 152 is wider than the central portion 158 in both the longitudinal direction x and the lateral direction y. As shown in FIG. 3, the first end 152 includes an underside 160 which extends from the central portion 158 in both the longitudinal direction x and the lateral direction y. The second end 154 of the on/off valve 150, in turn, is also wider than the central portion 158 in at least one of the longitudinal direction x and the lateral direction y. For instance, in the present embodiment, the second end 154 is wider than the central portion 158 along the lateral direction lateral direction y.

Furthermore, as best shown in FIG. 4, the second end 154 of the on/off valve 150 can include at least one elastically flexible clipping arm 162 configured to flex inward (in the lateral direction y) for purposes that will be described hereinafter. Specifically, the on/off valve 150 of the present embodiment includes two elastically flexible clipping arms 162 arranged on respective opposite sides of the second end 154 of the on/off valve 150, facing away from one another. The two clipping arms 162 are configured to flex toward and away from one another, and are elastically biased to flex away from one another. Each clipping arm 162 includes a stem 164, an outer sloped surface 166, an underside 168 and an end surface 170. A slit or gap 171 separates each clipping arm 162 from a central portion 172 of the second end 154. The central portion 172 includes an end surface 174. Preferably, the end surface 174 of the central portion 172 is generally coplanar with the end surfaces 170 of the clipping arms 162, as shown. The end surface 170 of the clipping arms 162 and/or the end surface 174 of the central portion 172 can be provided with texture or ridges 176 to increase the friction of a user's finger against the end surfaces 170 and/or 174 and facilitate pushing the end surface 170 and/or 174 towards the tip body 120 in the transverse direction z. Similarly, an end surface 178 of the first end 152 of the on/off valve 150 can include texture or ridges 180 to increase the friction of a user's finger against the end surface 178 and facilitate pushing the end surface 178 towards the tip body 120 in the transverse direction z.

The on/off valve 150 is preferably formed into a single-piece, plastic body, preferably by plastic injection molding. In turn, the tip body 120 is also preferably made of plastic, such as by plastic injection molding. In some embodiments, non-latex plastic can be used. The tip assembly 110 (i.e. the tip body 120 and on/off valve 150) is disposable so that the tip assembly 110 can be replaced as appropriate between patients.

Figure 5:
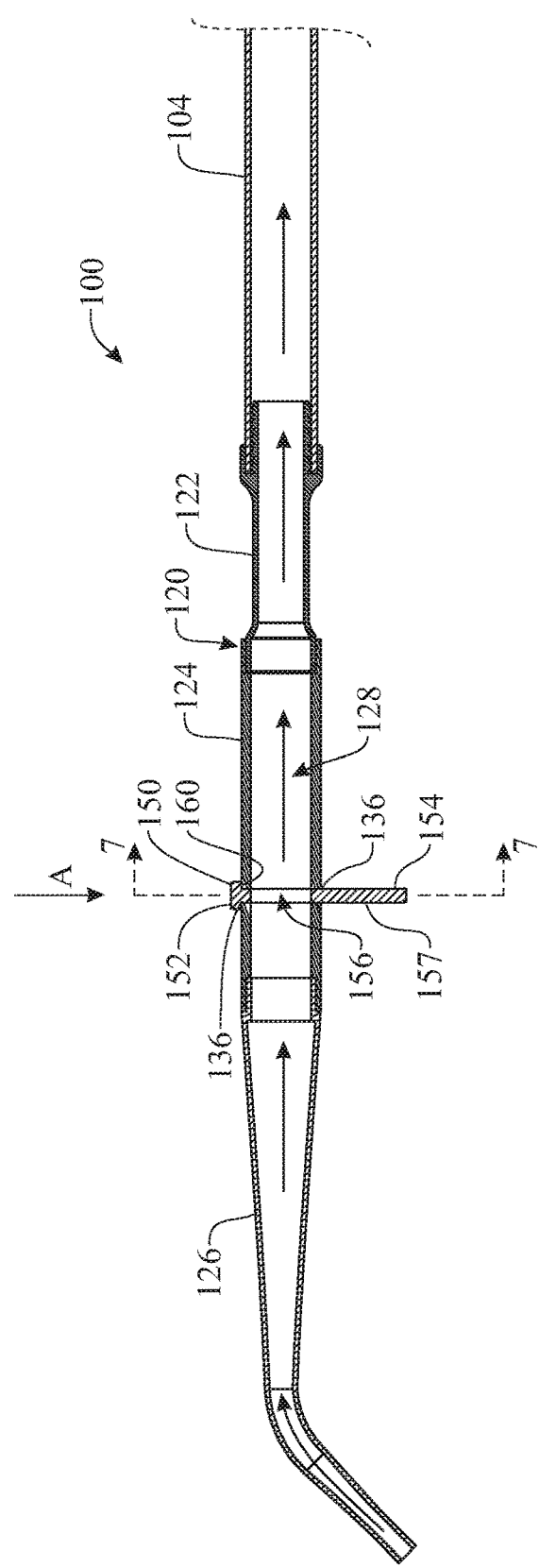
FIG. 5 presents a cross-sectional side elevation view of the saliva ejector system in an open position, the cross-section taken along a same plane as that of FIG. 6, with the on/off valve in a first transverse position allowing fluid to pass through a through bore of the on/off valve and into the tubing.

Operation of the saliva evacuator system 100 is described hereinafter with reference to FIGS. 1 and 5-8. Initially, a dental practitioner switches the vacuum pump 102 on, so that the vacuum pump 102 begins generating a depression or vacuum within the tubing 104 and the tip assembly 110. The practitioner then pushes the on/off valve 150 in the direction of arrow A to a first transverse position relative to the tip body 120 illustrated in FIGS. 5 and 7. In this first transverse position of the on/off valve 150, the through hole 156 of the on/off valve 150 is longitudinally aligned with the internal space 128 of the tip body 120 allowing fluid to pass through the through hole 156. In addition, in this first transverse position, the first end 152 of the on/off valve 150 protrudes outwardly from a first side of the valve support portion 124 of the tip body 120, and the first end 152 of the on/off valve 150 (and, more particularly, the underside 160) rests against the tip body 120 stopping the on/off valve 150 from being removed from the tip body 120 in the event that a continued pushing or puling force is exerted on the on/off valve 150 in the direction of arrow A. Furthermore, in this first transverse position, the second end 154 of the on/off valve 150 protrudes outwardly from an opposite side of the valve support portion 124 of the tip body 120, facilitating the pushing of the on/off valve 150 to a second transverse position shown in FIGS. 6 and 8. In the situation of FIGS. 5 and 7, the saliva evacuator system 100 is open, and fluid is allowed to be suctioned from the mouth of the patient, through the tip body 120 and into the tubing 104.

Figure 6:
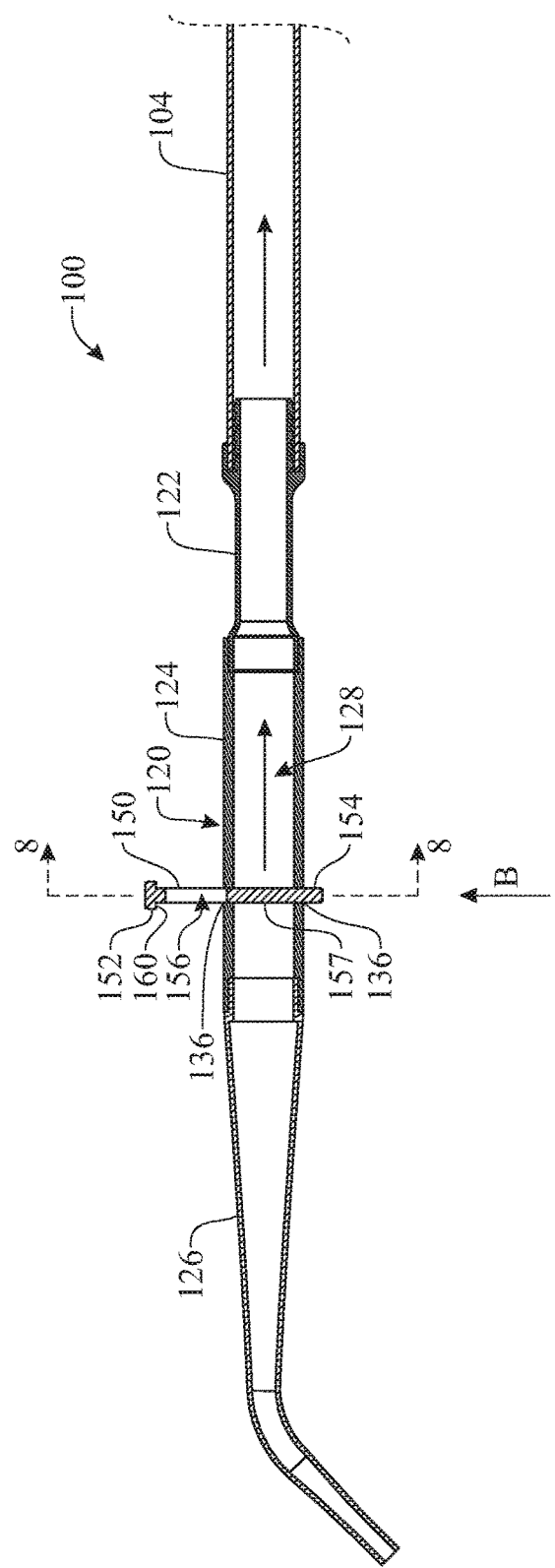
FIG. 6 presents a cross-sectional side elevation view of the saliva ejector system in a closed position, the cross section taken along section plane 6-6 indicated in FIG. 2, with the on/off valve in a second transverse position preventing fluid from passing through the tip body and into the tubing.
Figure 7:
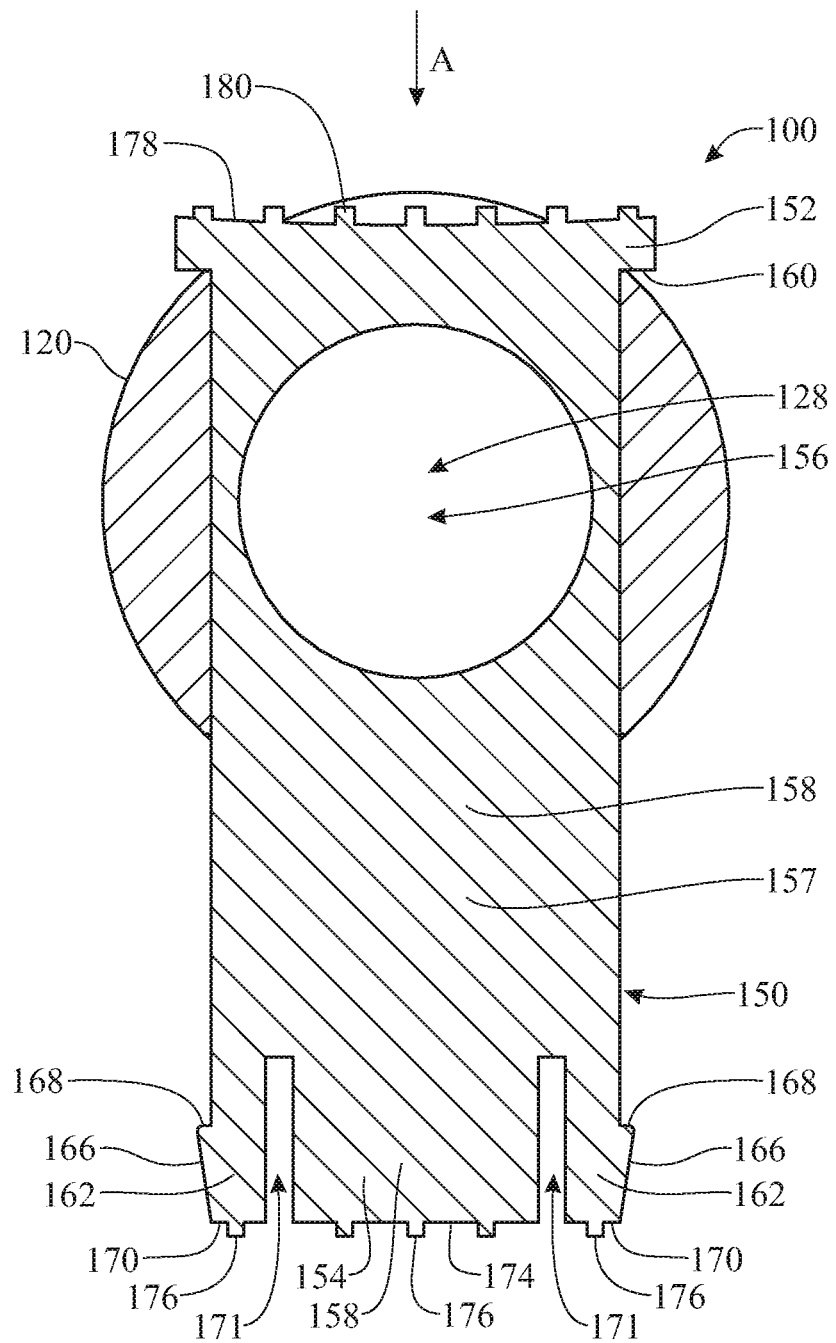
FIG. 7 presents a cross-sectional front elevation view of the assembly of FIG. 5, the cross section taken along section plant 7-7 indicated in FIG. 5.
Figure 8:
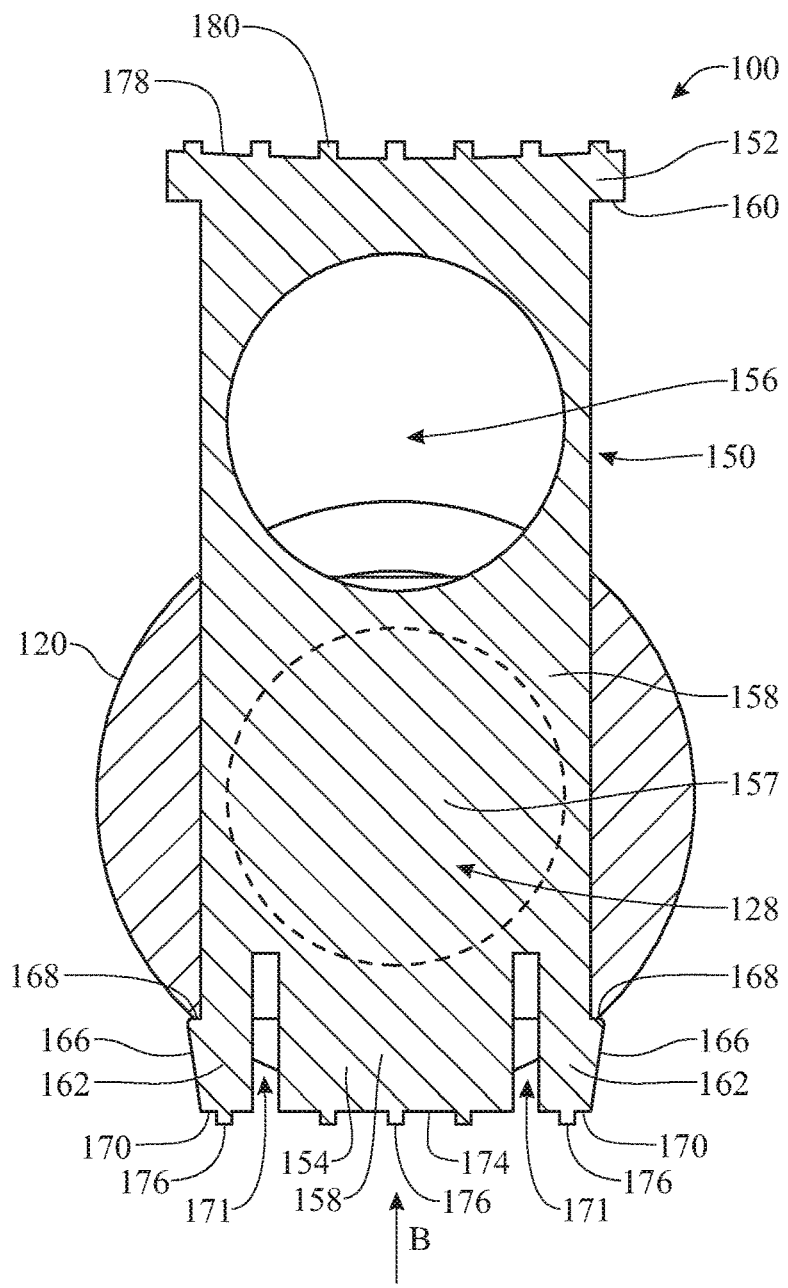
FIG. 8 presents a cross-sectional front elevation view of the assembly of FIG. 6, the cross section taken along section plant 8-8 indicated in FIG. 6.

When the practitioner wishes to interrupt fluid suction, the practitioner may push the on/off valve 150 in the direction of arrow B and transversely displace the on/off valve 150 relative to the top body 120 to a second transverse position relative to the tip body 120 shown in FIGS. 6 and 8. In this second transverse position, the through hole 156 of the on/off valve 150 is out of longitudinal alignment with the internal space 128 of the tip body 120 and a solid portion 157 of the on/off valve 150 is longitudinally aligned with the internal space 128, preventing fluid from passing through the on/off valve 150. The second end 154 of the on/off valve 150 protrudes from the tip body 120 and rests against the tip body 120, stopping the on/off valve 150 from being removed from the tip body 120 in the event that a continued pushing or puling force is exerted on the on/off valve 150 in the direction of arrow B. Furthermore, in this second transverse position, the first end 152 of the on/off valve 150 protrudes outwardly from the opposite side of the valve support portion 124 of the tip body 120, facilitating the pushing of the on/off valve 150 to the first transverse position shown in FIGS. 5 and 7 and described heretofore. In the situation of FIGS. 6 and 8, the saliva evacuator system 100 is closed, and fluid is prevented from being suctioned through the tip body 120 and into the tubing 104.

It should be noted that the on/off valve 150 is located away from the distal opening 134 of the tip portion 126 and does not get inserted into the mouth of the patient. This allows the on/off valve 150 to be turned on or off while the saliva ejector tip assembly 110 remains in the mouth of the patient. Also, because the on/off valve 150 is a push valve, it can easily be operated with only one hand of the dental practitioner. This allows the dental practitioner to control the saliva evacuator system 100 with one hand while holding or operating another dental tool with the other hand.

In summary, the saliva evacuator system 100 can selectively and reversibly adopt the open position of FIGS. 5 and 7 and the closed position of FIGS. 6 and 8 by easily pushing the on/off valve 150 transversely, while the on/off valve 150 is retained onto the tip body 120 by the stopping effect provided by the outwardly-protruding first and second ends 152 and 154 of the on/off valve 150.

The on/off valve 150 disclosed herein provides additional advantages. For example, assembly of the on-off valve 150 onto the tip body 120 is facilitated by the elastically flexible clipping arms 162. Specifically, as shown in FIG. 3, the on/off valve 150 can be assembled onto the tip body 120 by inserting the on/off valve 150, second end first, through the slots 136 of the tip body 120. As the second end 154 of the on/off valve 150 begins to be inserted into a slot 136, the outer sloped surfaces 166 of the clipping arms 162 contact the tip body 120, and the tip body 120 exerts a reaction force on the outer sloped surfaces 166 which causes the clipping arms 162 to flex inward, i.e. towards one another. In flexing inward, the width of the second end 154 of the on/off valve 150 is reduced and the second end 154 is able to pass through the slots 136. Once the second end 136 protrudes outwardly from the opposite side of the valve support portion 124, the reaction force ceases and the clipping arms 162 automatically flex outward, i.e. away from one another. This increases the width of the second end 154 and causes the second end to eventually become wider than the adjacent slot 136 and the clipping arms 162 to clip the on/off valve 150 onto the tip body 120 (the underside 168 of the clipping arms 162 providing a stopping effect against the tip body 120).

Figure 9:
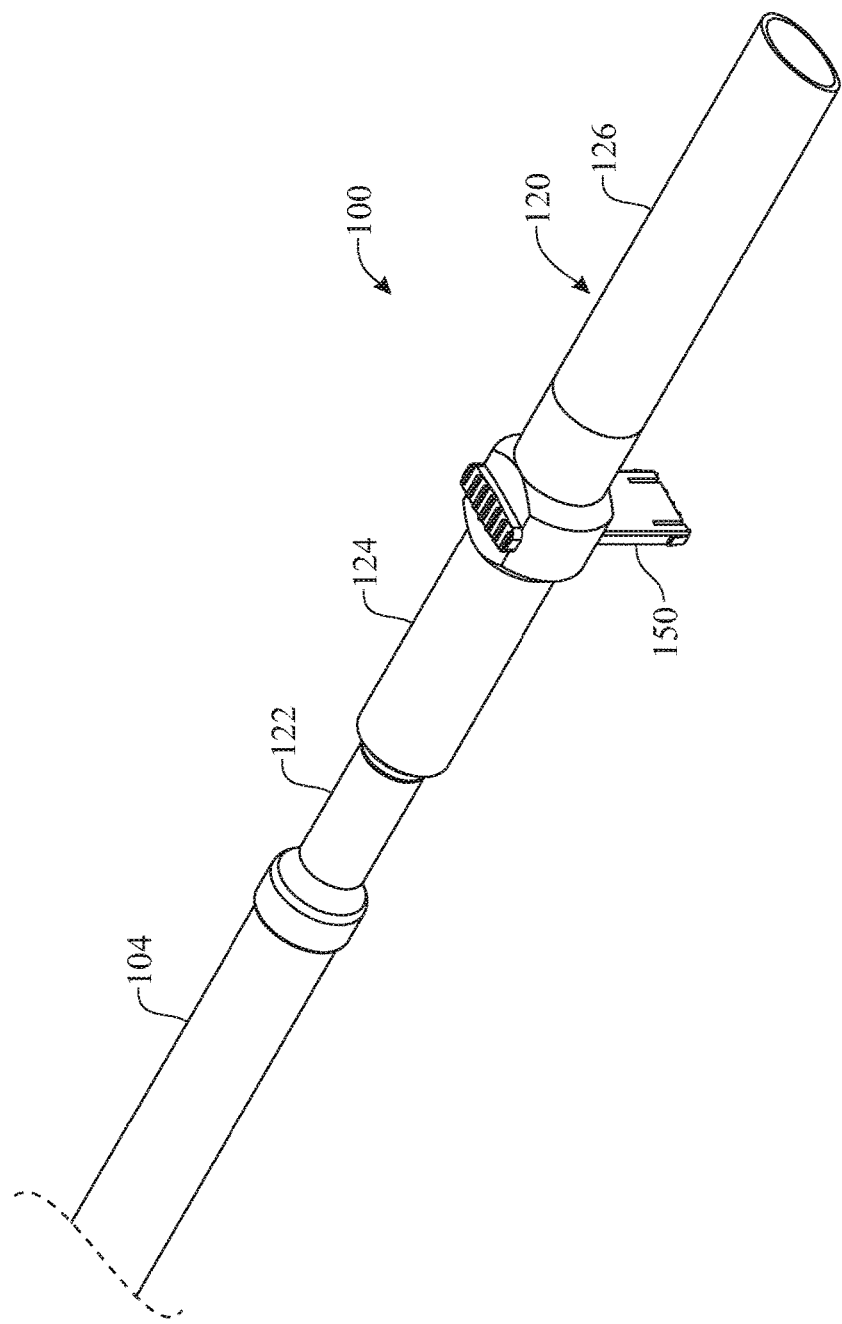
FIG. 9 presents a top front isometric assembled view of a distal end of a saliva evacuator system in accordance with the present invention, the tip body comprising a high volume ejector (HVE) tip.

The illustration of FIG. 9 shows a variant of the tip assembly 110 in which the tip portion 126 of the tip body 120 is a high-volume evacuator (HVE) tip, of the type used for instance for general dental aspiration of large particles to include tooth fragments, metals, resins, porcelain and fluids. Preferably, as shown, a same valve support portion 124 can receive, or be attached to, different tip portions 126. Alternatively or additionally, the saliva evacuator system 100 may come with more than one adapter 122, allowing to connect a same valve support portion 124 to tubings 104 having different diameters. Thus, the tip assembly 110 of the present invention can provide a disposable tip which is sufficiently versatile to cover most applications and needs.

In summary, the saliva evacuator system 100 provides an easy to manufacture, cost effective and disposable saliva evacuating kit, in which the valve and tip body are integrated with one another and disposable. Furthermore, the saliva evacuator system is versatile, as the tip portion of the tip body can be interchanged from a high volume evacuator to a surgical evacuator, and the adapter can be interchanged to adjust to different tubing diameters.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A saliva evacuator system for removing saliva from a patient's mouth, comprising:
   a vacuum pump;
   a tubing connected to the vacuum pump;
   a hollow tip assembly removably attachable to a distal end of the tubing, the tip assembly comprising a hollow tip body delimiting an internal space, wherein the internal space extends in a longitudinal direction through a length of the tip body from a proximal end of the tip body to a distal end of the tip body, the tip assembly further comprising an on/off valve formed as a single-piece body by plastic injection molding, wherein the on/off valve movably extends transversely to the longitudinal direction through the internal space and through opposite side slots formed in the tip body, the on/off valve comprising a first end, an opposite, second end and a through hole, wherein the second end of the on/off valve comprises at least one elastically flexible clipping arm configured to flex inward allowing the on/off valve to be inserted through the slots of the tip body and elastically biased to return to an outward position, wherein
   the saliva evacuator system is configured to selectively and reversibly adopt the following positions by transversely moving the on/off valve relative to the tip body:
   an open position, in which the on/off valve is moved to a first transverse position relative to the tip body such that the through hole of the on/off valve is longitudinally aligned with the internal space of the tip body allowing fluid to pass therethrough, and further in which the on/off valve protrudes from opposite transverse sides of the tip body and the first end of the on/off valve rests against the tip body stopping the on/off valve from being removed from the tip body, and
   a closed position, in which the on/off valve is moved to a second transverse position relative to the tip body such that the through hole of the on/off valve is out of longitudinal alignment with the internal space of the tip body and a solid portion of the on/off valve is longitudinally aligned with said internal space preventing fluid from passing therethrough, and further in which the on/off valve protrudes from opposite transverse sides of the tip body and the at least one clipping arm of the second end of the on/off valve rests against the tip body stopping the on/off valve from being removed from the tip body.

2. The saliva evacuator system of claim 1, wherein the at least one elastically flexible clipping arm includes two elastically flexible clipping arms arranged on respective opposite sides of the second end of the on/off valve.

3. The saliva evacuator system of claim 2, wherein the elastically flexible clipping arms are arranged on respective opposite sides of the second end of the on/off valve, facing away from one another.

4. The system of claim 1, wherein the tip body comprises one of a saliva ejector tip, a high-volume evacuator tip and a surgical high volume evacuator tip.

5. The system of claim 1, wherein the tip body comprises a valve support portion and a first tip portion, wherein the valve support portion carries the on/off valve and the first tip portion is removably attached to the valve support portion.

6. The system of claim 5, wherein the tip portion is one of a saliva ejector tip, a high-volume evacuator tip and a surgical high volume evacuator tip.

7. The system of claim 1, wherein the tip body comprises a valve support portion and two or more tip portions, wherein the valve support portion carries the on/off valve and the two or more tip portions are removably and interchangeably attachable to the valve support portion.

8. The system of claim 7, wherein the two or more tip portions include two or more of a saliva ejector tip, a high-volume evacuator tip and a surgical high volume evacuator tip.

9. The system of claim 1, further comprising an adapter, removably connectable to the tubing and to the tip body.

10. A tip assembly for a saliva evacuator system for removing saliva from a patient's mouth, the tip assembly comprising:
    a hollow tip body delimiting an internal space, wherein the internal space extends in a longitudinal direction through a length of the tip body from a proximal end of the tip body to a distal end of the tip body, the tip assembly further comprising an on/off valve formed as a single-piece body by plastic injection molding, wherein the on/off valve movably extends transversely to the longitudinal direction through the internal space and through opposite side slots formed in the tip body, the on/off valve comprising a first end, an opposite, second end and a through hole, wherein the second end of the on/off valve comprises at least one elastically flexible clipping arm configured to flex inward allowing the on/off valve to be inserted through the slots of the tip body and elastically biased to return to an outward position, wherein
    the tip assembly is configured to selectively and reversibly adopt the following positions by transversely moving the on/off valve relative to the tip body:
    an open position, in which the on/off valve is moved to a first transverse position relative to the tip body such that the through hole of the on/off valve is longitudinally aligned with the internal space of the tip body allowing fluid to pass therethrough, and further in which the on/off valve protrudes from opposite transverse sides of the tip body and the first end of the on/off valve rests against the tip body stopping the on/off valve from being removed from the tip body, and a closed position, in which the on/off valve is moved to a second transverse position relative to the tip body such that the through hole of the on/off valve is out of longitudinal alignment with the internal space of the tip body and a solid portion of the on/off valve is longitudinally aligned with said internal space preventing fluid from passing therethrough, and further in which the on/off valve protrudes from opposite transverse sides of the tip body and the at least one clipping arm of the second end of the on/off valve rests against the tip body stopping the on/off valve from being removed from the tip body.

11. The tip assembly of claim 10, wherein the at least one elastically flexible clipping arm includes two elastically flexible clipping arms arranged on respective opposite sides of the second end of the on/off valve.

12. The tip assembly of claim 11, wherein the elastically flexible clipping arms are arranged on respective opposite sides of the second end of the on/off valve, facing away from one another.

13. The tip assembly of claim 10, wherein the tip body comprises a valve support portion and a first tip portion, wherein the valve support portion carries the on/off valve and the first tip portion is removably attached to the valve support portion.

14. The tip assembly of claim 13, wherein the tip portion is one of a saliva ejector tip, a high-volume evacuator tip and a surgical high volume evacuator tip.

15. The tip assembly of claim 10, wherein the tip body comprises a valve support portion and two or more tip portions, wherein the valve support portion carries the on/off valve and the two or more tip portions are removably and interchangeably attachable to the valve support portion.

16. The tip assembly of claim 15, wherein the two or more tip portions include two or more of a saliva ejector tip, a high-volume evacuator tip and a surgical high volume evacuator tip.

17. A tip assembly for a saliva evacuator system for removing saliva from a patient's mouth, the tip assembly comprising:

a hollow tip body delimiting an internal space, wherein the internal space extends in a longitudinal direction through a length of the tip body from a proximal end of the tip body to a distal end of the tip body, the tip assembly further comprising an on/off valve formed as a single-piece body by plastic injection molding, wherein the on/off valve movably extends transversely to the longitudinal direction through the internal space and through opposite side slots formed in the tip body, the on/off valve comprising a first end, an opposite, second end and a through hole, wherein the tip assembly is configured to selectively and reversibly adopt the following positions by transversely moving the on/off valve relative to the tip body:

an open position, in which the on/off valve is moved to a first transverse position relative to the tip body such that the through hole of the on/off valve is longitudinally aligned with the internal space of the tip body allowing fluid to pass therethrough, and further in which the on/off valve protrudes from opposite transverse sides of the tip body and the first end of the on/off valve rests against the tip body stopping the on/off valve from being removed from the tip body, and an closed position, in which the on/off valve is moved to a second transverse position relative to the tip body such that the through hole of the on/off valve is out of longitudinal alignment with the internal space of the tip body and a solid portion of the on/off valve is longitudinally aligned with said internal space, preventing fluid from passing therethrough, and further in which the on/off valve protrudes from opposite transverse sides of the tip body and the second end of the on/off valve rests against the tip body stopping the on/off valve from being removed from the tip body; wherein the second end of the on/off valve comprises two elastically flexible clipping arms configured to flex inward allowing the on/off valve to be inserted through the slots of the tip body and elastically biased to return to an outward position for the resting of the clipping arms on the tip body when the tip assembly is in the closed position.

18. The tip assembly of claim 17, wherein the elastically flexible clipping arms are arranged on respective opposite sides of the second end of the on/off valve, facing away from one another.

* * * * *